United States Patent
Kelly et al.

(10) Patent No.: US 9,785,892 B2
(45) Date of Patent: Oct. 10, 2017

(54) AUTOMATING DISPLAYS BASED ON ADMISSIONS, DISCHARGES, AND TRANSFERS

(75) Inventors: Lisa Kelly, Overland Park, KS (US); Stephanie L. Rogers, Kansas City, MO (US); Jared Wayne Fordham, Independence, MO (US); Amanda Buckley, Olathe, KS (US); Robert Farr, Jr., Liberty, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 187 days.

(21) Appl. No.: 13/159,603

(22) Filed: Jun. 14, 2011

(65) Prior Publication Data
US 2012/0323588 A1    Dec. 20, 2012

(51) Int. Cl.
*G06Q 10/00*      (2012.01)
*G06Q 50/00*      (2012.01)
*G06Q 50/22*      (2012.01)

(52) U.S. Cl.
CPC .............. *G06Q 10/00* (2013.01); *G06Q 50/22* (2013.01)

(58) Field of Classification Search
CPC ........ G06Q 50/22; G06Q 50/24; G06Q 40/08; G06Q 10/10; G06F 19/327; G06F 19/322; A61B 5/002
See application file for complete search history.

(56) References Cited

U.S. PATENT DOCUMENTS

| | | | |
|---|---|---|---|
| 7,746,218 B2 * | 6/2010 | Collins et al. | 340/286.07 |
| 2002/0120472 A1 * | 8/2002 | Dvorak et al. | 705/3 |
| 2003/0074222 A1 * | 4/2003 | Rosow et al. | 705/2 |
| 2004/0210548 A1 * | 10/2004 | Ketcherside, Jr. et al. | 706/924 |
| 2005/0043968 A1 * | 2/2005 | Sauerwald | 705/2 |
| 2011/0205062 A1 * | 8/2011 | Pesot et al. | 340/573.1 |

\* cited by examiner

*Primary Examiner* — Michelle L Le
(74) *Attorney, Agent, or Firm* — Shook, Hardy & Bacon L.L.P.

(57) ABSTRACT

Systems, methods, computer-readable media, and graphical user interfaces for automating displays based on admissions, transfers, and discharges are provided. In embodiments, admission notifications that patients have been admitted to rooms in a healthcare facility are received. Information is accessed for the patients admitted to the rooms. The information for the patients is automatically displayed, without user intervention, to clinicians in the corresponding rooms.

19 Claims, 14 Drawing Sheets

| IAWARE CRITICAL CARE | | | | | | |
|---|---|---|---|---|---|---|
| IAWARE HELP | | | | | | |
| MYLIST | PATIENT SEARCH | UNIT INFUSION STATUS | ICU SUMMARY | MEDS REVIEW | | | | |
| | VITALS/INFUSION (24HR) | I/O (7 DAY) BLOOD GLUCOSE | | | | | | |

MYLIST

ENTER A LOCATION OR TAG NAME. (ENTER ONLY ALPHANUMERIC CHARACTERS, SPACES, OR UNDERSCORES.)

[ ] 🔍 FIND ENCOUNTERS        LIST RESULTS AS OF  🕒 0 MINUTES AGO

| 2 EAST | CHILDREN'S HOSPITAL | | | | | |
|---|---|---|---|---|---|---|
| NAME | MRN | LOCATION | ADMIT DATE/TIME | FIN | TAGS CURRENTLY ASSIGNED | |
| GONZOLES, MIKE | 009-074 | 2 EAST/2145 | 9/27/2009 09:35 | 17784 | PULMONARY_CONSULT, SURGERY_SERVICE | |
| HOLMES, RICHARD | 310989 | 2 EAST/2151 | 10/1/2009 09:00 | 78623962 | BRENDA_PATIENTS, PULMONARY_CONSULT | |
| LARUE, CHANTELLE | 453216 | 2 EAST/2150 | 9/3/2009 09:35 | 77634589 | BRENDA_PATIENTS, SURGERY_SERVICE | |
| LESTER, SUMMER | 453189 | 2 EAST/2152 | 9/15/2009 07:00 | 12876190 | BRENDA_PATIENTS, PULMONARY_CONSULT, SURGERY_SERVICE | |
| MERRIWEATHER, ROBYN | 289547 | 2 EAST/2146 | 9/25/2009 10:00 | 33901872 | BRENDA_PATIENTS | |
| RODRIGUEZ, JOSE | 845325 | 2 EAST/2148 | 9/30/2009 08:00 | 88743578 | PULMONARY_CONSULT | |
| SCHMITT, EUGENE | 237698 | 2 EAST/2153 | 9/16/2009 08:00 | 33146723 | PULMONARY_CONSULT | |
| SYDNEY, WALKER | 875124 | 2 EAST/2149 | 10/4/2009 09:00 | 90876432 | SURGERY_SERVICE | |
| WHITE, OLIVER | 778412 | 2 EAST/2147 | 10/3/2009 09:00 | 90763217 | BRENDA_PATIENTS, PULMONARY_CONSULT, SURGERY_SERVICE | |
| XEN, LIU | 461310 | 2 EAST/2154 | 10/4/2009 08:00 | 98120494 | BRENDA_PATIENTS, PULMONARY_CONSULT, SURGERY_SERVICE | |

ⓘ 🔔 NEW PATIENT ADMITTED IN 2145    LOCATION: 2145 SYSTEM TIME: 8/19/2010 10:09 CDT USER: MOCK@MOCKDOMAIN

FIG. 3.

| IAWARE CRITICAL CARE | | | | | — ☐ ✗ |
|---|---|---|---|---|---|
| IAWARE HELP | | | | | |

MYLIST  PATIENT SEARCH  UNIT INFUSION STATUS | ICU SUMMARY  MEDS REVIEW |
| VITALS/INFUSION (24HR)  I/O (7 DAY) BLOOD GLUCOSE |

MYLIST

ENTER A LOCATION OR TAG NAME. (ENTER ONLY ALPHANUMERIC CHARACTERS, SPACES, OR UNDERSCORES.)

| ⓘ [                    ] 🔍 FIND ENCOUNTERS | | | | LIST RESULTS AS OF  🔄 0 MINUTES AGO |
|---|---|---|---|---|

| 2 EAST  CHILDREN'S HOSPITAL | | | | |
|---|---|---|---|---|
| NAME | MRN | LOCATION | ADMIT DATE/TIME | FIN | TAGS CURRENTLY ASSIGNED |
| GONZOLES, MIKE | 009-074 | 2 EAST/2145 | 9/27/2009 09:35 | 17784 | PULMONARY_CONSULT, SURGERY_SERVICE |
| HOLMES, RICHARD | 310989 | 2 EAST/2151 | 10/1/2009 09:00 | 78623962 | BRENDA_PATIENTS, PULMONARY_CONSULT |
| LARUE, CHANTELLE | 453216 | 2 EAST/2150 | 9/3/2009 09:35 | 77634589 | BRENDA_PATIENTS, SURGERY_SERVICE |
| LESTER, SUMMER | 453189 | 2 EAST/2152 | 9/15/2009 07:00 | 12876190 | BRENDA_PATIENTS, PULMONARY_CONSULT, SURGERY_SERVICE |
| MERRIWEATHER, ROBYN | 289547 | 2 EAST/2146 | 9/25/2009 10:00 | 33901872 | BRENDA_PATIENTS |
| RODRIGUEZ, JOSE | 845325 | 2 EAST/2148 | 9/30/2009 08:00 | 88743578 | PULMONARY_CONSULT |
| SCHMITT, EUGENE | 237698 | 2 EAST/2153 | 9/16/2009 08:00 | 33146723 | PULMONARY_CONSULT |
| SYDNEY, WALKER | 875124 | 2 EAST/2149 | 10/4/2009 09:00 | 90876432 | SURGERY_SERVICE |
| WHITE, OLIVER | 778412 | 2 EAST/2147 | 10/3/2009 09:00 | 90763217 | BRENDA_PATIENTS, PULMONARY_CONSULT, SURGERY_SERVICE |
| XEN, LIU | 461310 | 2 EAST/2154 | 10/4/2009 08:00 | 98120494 | BRENDA_PATIENTS, PULMONARY_CONSULT, SURGERY_SERVICE |

NEW PATIENT ADMITTED IN 2145                                    ⊗

OPEN: GONZOLES, MIKE
DOB: 1/4/1954   MRN: 009-074   2 EAST/2145

🔔 NEW PATIENT ADMITTED IN 2145       LOCATION: 2145  SYSTEM TIME: 8/19/2010 10:10 CDT  USER: MOCK@MOCKDOMAIN

AUTOMATING DISPLAYS BASED ON ADMISSIONS, DISCHARGES, AND TRANSFERS

BACKGROUND

Patient medical information, such as that contained in medical record, allows health care providers to provide continuity of care to patients. Thus, it is critical for clinicians providing care to patients to review and update each patient's medical record. The growth in access to and utilization of electronic medical records by healthcare providers and facilities has significantly reduced the time and organization efforts required by paper medical records. Unfortunately, this growth has introduced new problems. Medical records associated with the incorrect patient are often mistakenly viewed without knowledge by the clinician. For example, the medical record may be left open in a room after a patient is discharged or transferred and the clinician forgets to close the discharged or transferred patient's medical record and open the newly admitted patient's medical record. In other cases, the clinician may simply open the medical record for the wrong patient. This problem is compounded when the clinician enters information into the incorrect patient's medical record.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to methods, systems, graphical user interfaces, and computer readable media for facilitating automating displays based on admissions, discharges, and transfers. In one embodiment, computer storage media having computer-executable instructions embodied thereon that, when executed, facilitate a method of automatically opening and closing information associated with a patient. An admission notification that a patient has been admitted to a room in a healthcare facility is received. Information for the patient admitted to the room is accessed. The information for the patient is displayed to a clinician in the room automatically, without user intervention.

In another embodiment, a computer system, comprising a processor coupled to a computer storage medium, the computer storage medium having stored thereon a plurality of computer software components executable by the processor, for automating displays based on admissions, discharges, and transfers is provided. A notification component receives a notification that a patient has been admitted to a room or bed. An information component retrieves patient information corresponding to the notification. A ready component determines that a clinician is ready to view the information. A display component automatically displays the information to the clinician. A discharge/transfer notification component notifies the clinician that the patient has been discharged or transferred. A finish component determines if a clinician is finished with the information. A close component automatically closes the information when the clinician is finished.

In another embodiment, computer storage media having computer-executable instructions embodied thereon that, when executed, produce a graphical user interface (GUI) to facilitate automating displays based on admissions, discharges, and transfers. A first display area displays admission information for a patient that has been admitted to a room in a healthcare facility. A second display area displays an opening progress information message notifying the clinician that information for the patient will be opened and provides the clinician an opportunity to cancel opening the information if the clinician is not ready. A third display area displays the information for the patient. A fourth display area displays a notification that the patient has been discharged or transferred from the room or bed. A fifth display area displays a closing progress information message notifying the clinician that information for the patient will be closed and provides the clinician an opportunity to cancel closing the information if the clinician is not ready.

BRIEF DESCRIPTION OF THE DRAWINGS

Embodiments are described in detail below with reference to the attached drawing figures, wherein:

FIGS. 3-13 are illustrative screen displays in accordance with embodiments of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

Having briefly described embodiments of the present invention, an exemplary operating environment suitable for use in implementing embodiments of the present invention is described below.

Figure 1:
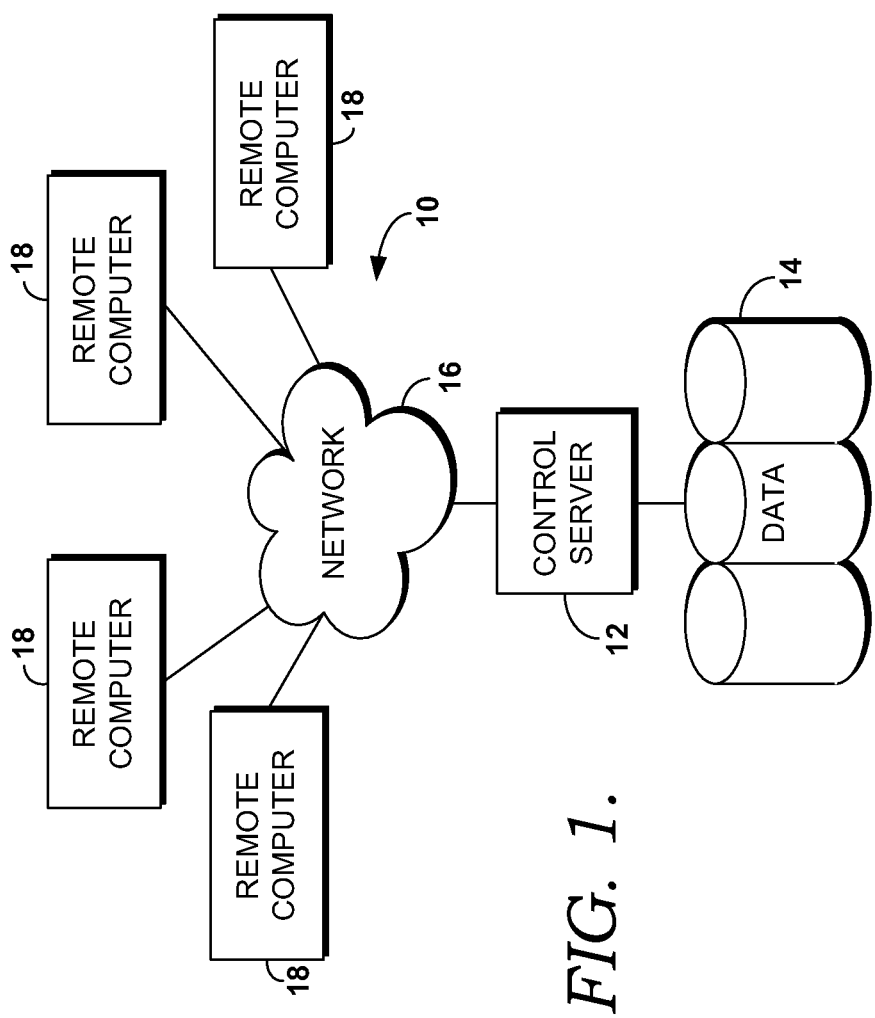
FIG. 1 is a block diagram of an exemplary computing environment suitable for use in implementing embodiments of the present invention.

Referring to the drawings in general, and initially to FIG. 1 in particular, an exemplary computing system environment, a medical information computing system environment, with which embodiments of the present invention may be implemented is illustrated and designated generally as reference numeral 20. It will be understood and appreciated by those of ordinary skill in the art that the illustrated medical information computing system environment 10 is merely an example of one suitable computing environment and is not intended to suggest any limitation as to the scope of use or functionality of the invention. Neither should the medical information computing system environment 10 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, handheld or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 10 includes a general purpose computing device in the form of a control server 12. Components of the control server 12 may include, without limitation, a processing unit, internal system memory, and a suitable system bus for coupling various system components, including database cluster 14, with the control server 12. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 12 typically includes therein, or has access to, a variety of computer-readable media, for instance, database cluster 14. Computer-readable media can be any available media that may be accessed by server 12, and includes volatile and nonvolatile media, as well as removable and non-removable media. By way of example, and not limitation, computer-readable media may include computer storage media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 12. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 14, provide storage of computer-readable instructions, data structures, program modules, and other data for the control server 12. The control server 12 may operate in a computer network 16 using logical connections to one or more remote computers 18. Remote computers 18 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as intensivists, surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 18 may also be physically located in non-traditional medical care environments so that the entire health care community may be capable of integration on the network. The remote computers 18 may be personal computers, servers, routers, network PCs, peer devices, other common network nodes, or the like, and may include some or all of the elements described above in relation to the control server 12. The devices can be personal digital assistants or other like devices.

Exemplary computer networks 16 may include, without limitation, local area networks (LANs) and/or wide area networks (WANs). Such networking environments are commonplace in offices, enterprise-wide computer networks, intranets, and the Internet. When utilized in a WAN networking environment, the control server 12 may include a modem or other means for establishing communications over the WAN, such as the Internet. In a networked environment, program modules or portions thereof may be stored in association with the control server 12, the database cluster 14, or any of the remote computers 18. For example, and not by way of limitation, various application programs may reside on the memory associated with any one or more of the remote computers 18. It will be appreciated by those of ordinary skill in the art that the network connections shown are exemplary and other means of establishing a communications link between the computers (e.g., control server 12 and remote computers 18) may be utilized.

In operation, a clinician may enter commands and information into the control server 12 or convey the commands and information to the control server 12 via one or more of the remote computers 18 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 12. In addition to a monitor, the control server 12 and/or remote computers 18 may include other peripheral output devices, such as speakers and a printer.

Although many other internal components of the control server 12 and the remote computers 18 are not shown, those of ordinary skill in the art will appreciate that such components and their interconnection are well known. Accordingly, additional details concerning the internal construction of the control server 12 and the remote computers 18 are not further disclosed herein.

Figure 2:
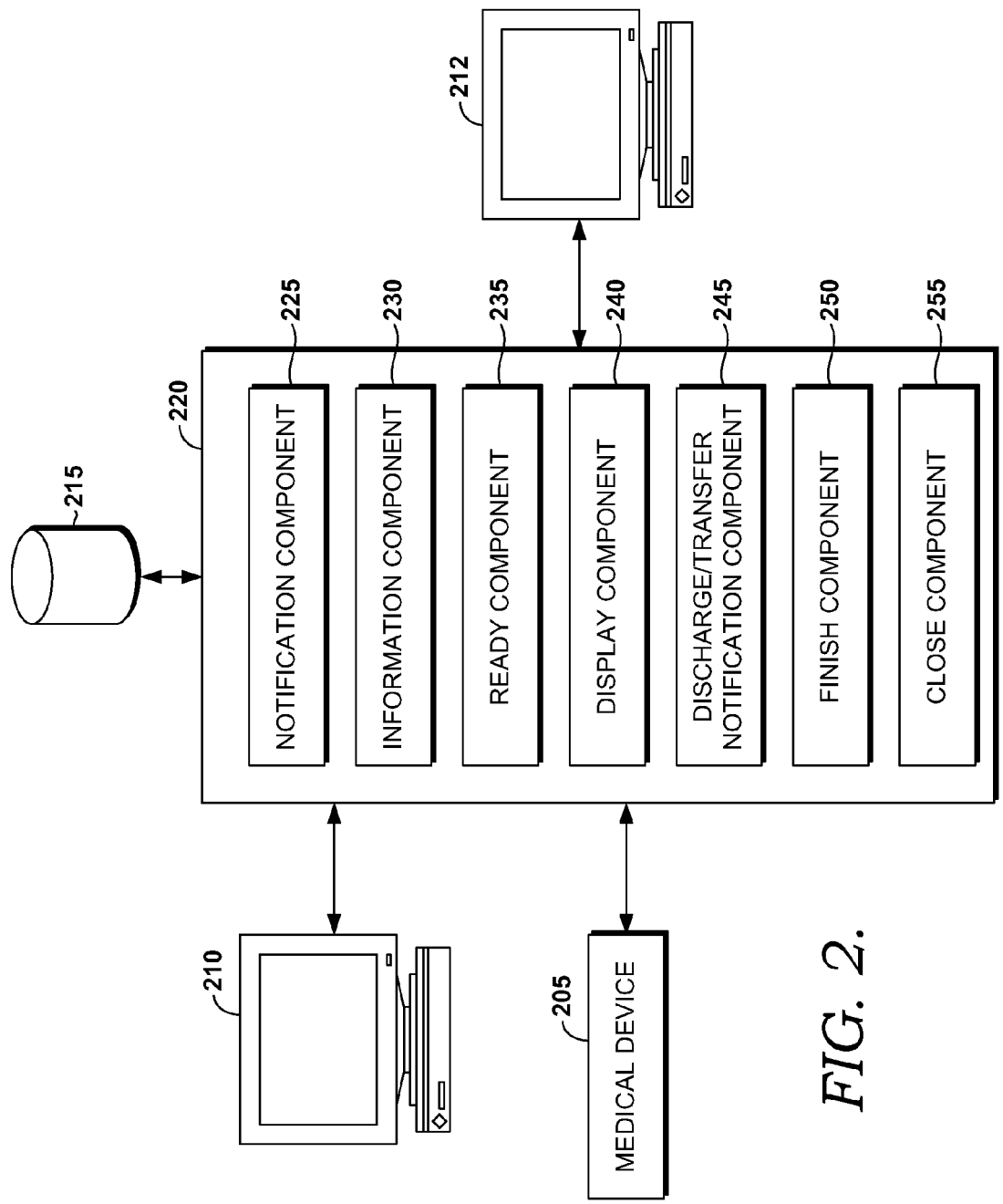
FIG. 2 is an exemplary system architecture suitable for use in implementing embodiments of the present invention.

With reference to FIG. 2, a block diagram is illustrated that shows an exemplary computing system architecture for automatically opening and closing patient information. It will be appreciated that the computing system architecture shown in FIG. 2 is merely an example of one suitable computing system and is not intended as having any dependency or requirement related to any single module/component or combination of modules/components.

The computing system includes one or more medical devices 205, admission, discharge, and transfer (ADT)

workstation 210, graphical display device 212, datastore 215, and automated displays module 220. Data elements are received from medical devices 205. A medical device 205 may be any device, stationary or otherwise, that may be used to treat, diagnose, monitor, or measure aspects of a patient in a hospital, doctor's office, etc. For exemplary purposes only and not limitation, medical devices include cardiac monitors, cardiac output monitors, ICP monitors, ventilators, pumps (e.g., infusion pumps, balloon pumps), and the like. As such, these medical devices generate various data (e.g., heart-rate changes) that is communicated to datastore 215.

Datastore 215 contains a variety of information data for the patient in a patient's electronic medical record (EMR). As utilized herein, the acronym "EMR" is not meant to be limiting, and may broadly refer to any or all aspects of the patient's medical record rendered in a digital format. Generally, the EMR is supported by systems configured to co-ordinate the storage and retrieval of individual records with the aid of computing devices. As such, a variety of types of healthcare-related information may be stored and accessed in this way. By way of example, the EMR may store one or more of the following types of information: patient demographic; medical history (e.g., examination and progress reports of health and illnesses); medicine and allergy lists/immunization status; laboratory test results, radiology images (e.g., X-rays, CTs, MRIs, etc.); evidence-based recommendations for specific medical conditions; a record of appointments and physician's notes; billing records; and data received from an associated medical device. Accordingly, systems that employ EMRs reduce medical errors, increase physician efficiency, and reduce costs, as well as promote standardization of healthcare. Graphical display device 212 may be a monitor, computer screen, project device or other hardware device for displaying output and capable of displaying graphical user interfaces.

Automated displays module 220 receives and displays data from datastore 215 and/or one or more medical devices 205 for a patient. Automated displays module 220 may reside on one or more computing devices, such as, for example, the control server 12 described above with reference to FIG. 1. By way of example, the control server 12 includes a computer processor and may be a server, personal computer, desktop computer, laptop computer, handheld device, mobile device, consumer electronic device, or the like.

Automated displays module 220 comprises notification component 225, information component 230, ready component 235, display component 240, discharge/transfer notification component 245, finish component 250, and a close component 255. In various embodiments, automated displays module 220 includes a location component (not shown in FIG. 2), a not ready component (not shown in FIG. 2), a new patient component (not shown in FIG. 2), a new information component (not shown in FIG. 2), a mismatch component (not shown in FIG. 2), and a reminder component (not shown in FIG. 2). In one embodiment, a location component determines the location of the graphical display device 212. Notification component 225 receives a notification that a patient has been admitted to a room or bed. In one embodiment, the notification originates with the ADT workstation 210. In one embodiment, the notification originates from an ADT workstation 210 within the room the patient is being admitted to. In one embodiment, the notification originates from an ADT workstation 210 not within the room the patient is being admitted to. In one embodiment, the ADT workstation 210 and the graphical display device 212 are the same device. It will be appreciated that while automated displays module 220 is depicted as being connected to a single medical device 205 and datastore 215, automated displays module 220 may receive data from multiple medical devices and/or datastores including for multiple patients at multiple locations.

The information retrieved by information component 230 includes data and other information stored by datastore 215. In one embodiment, information component 225 may receive real-time data from the medical devices 210 via the datastore 215. In one embodiment, the patient is continuously monitored and new data points are sent to the information component 225 via the datastore 215 such that they may be plotted and displayed in a waveform quickly or in real-time. For clarity, real-time includes near real-time, taking into account latency or other typical delays between one or more devices communicating in a networked environment.

A ready component 235 determines that a clinician is ready to view the information. For example, the clinician may require additional time reviewing or inputting information into a previous patient's EMR. In this instance, the ready component determines that a clinician is not ready to view the information for a patient being admitted. In one embodiment, when the patient is admitted, the system prompts the clinician to determine if the clinician is ready. In another embodiment, the system detects that a clinician has not recently viewed or edited the information of a previous patient. In one embodiment, a not ready component keeps the information open until the clinician is finished. For example, the system may detect that a clinician has recently viewed or edited the data of the previous patient. A preconfigured time period is provided after the most recent interaction by the clinician before the ready component determines that the clinician is ready to view the information for the admitted patient.

A display component 240 automatically displays the information to the clinician. In one embodiment, no user intervention is necessary. Once the notification component 225 has received a notification that a patient has been admitted to the room, the information component 230 retrieves the patient information from the datastore 215 corresponding to the notification. The ready component 235 determines that the clinician is ready to view the information and the display component 240 automatically displays the information to the clinician. In one embodiment, after the information component 230 retrieves the information, the display component 240 automatically displays the information to the clinician, bypassing the ready component 235. In one embodiment, a mismatch component notifies the clinician if the displayed information does not match the patient that is registered to the room or bed. In one embodiment, the mismatch component compares the location from the location component to the notification from the notification to determine if the location corresponds to the room associated with the admitted patient. This prevents the clinician from reviewing incorrect information or editing the wrong patient's information.

A discharge/transfer notification component 245 notifies the clinician that the patient has been discharged or transferred. In one embodiment, a discharge or transfer event is received by the discharge transfer notification component 245 via the ADT workstation 210. This notification provides the clinician sufficient warning that the clinician needs to finish reviewing or editing the information.

A finish component 250 determines if the clinician is finished reviewing or editing the information. In one embodiment, the clinician is prompted to determine if the clinician is finished reviewing or editing the information. In one embodiment, the system detects that a clinician has not recently viewed or edited the information. In one embodiment, the finish component 250 warns the clinician that the information for the patient will automatically close after a preconfigured time has lapsed.

A close component 255 automatically closes the information when the clinician is finished. In one embodiment, the finish component is bypassed and the close component 255 automatically closes the information upon a discharge or transfer event. In one embodiment, the clinician is provided an opportunity to delay or prevent the close component 255 from automatically closing the information. In one embodiment, a reminder component reminds the clinician to close the information after the patient has been transferred or discharged.

In one embodiment, a new patient component notifies the clinician that a new patient has been assigned to the room or bed. This notification provides the clinician sufficient warning to finish reviewing or editing the information for the patient. In one embodiment, the clinician is provided an opportunity to continue reviewing or editing the information for the patient or switch to new patient information associated with the new patient. In one embodiment, a new information component automatically displays new patient information associated with the new patient.

Referring now to FIG. 3, in an illustrative screen display 300, an admission display area 310 displays admission information for a patient that has been admitted to a room in a healthcare facility. A location display area 315 displays the location of the graphical display device. The admission information includes a room number the patient was admitted to, and may include additional information, such as a patient name, a patient identifier, a clinician associated with the patient, a unit, a date or time, reason for admission, and the like. A list of patients display area 320, may also be displayed, in various embodiments, identifying patients in a particular location or vicinity, or patients assigned to a particular clinician. In one embodiment, the patient registered to the room the clinician is in is highlighted.

Referring now to FIG. 4, in an illustrative screen display 400, an admission display area 410 displays admission information for a patient that has been admitted to a room in a healthcare facility, as described above. Additional information 412 is available and displayed to a clinician by moving a cursor, in one embodiment, over the admission display area 410. In another embodiment, the additional information 412 is displayed to the clinician when the clinician selects the admission display area 410. In one embodiment, the additional information may include an option to open the information associated with the patient such that when the clinician selects the additional information or clicks in an appropriate section of the additional information, the information for that patient opens. A location display area 415 displays the location of the graphical display device. As described above, a list of patients display area 420 may also be displayed, in various embodiments, identifying patients in a particular location or vicinity, or patients assigned to a particular clinician.

Figure 5:
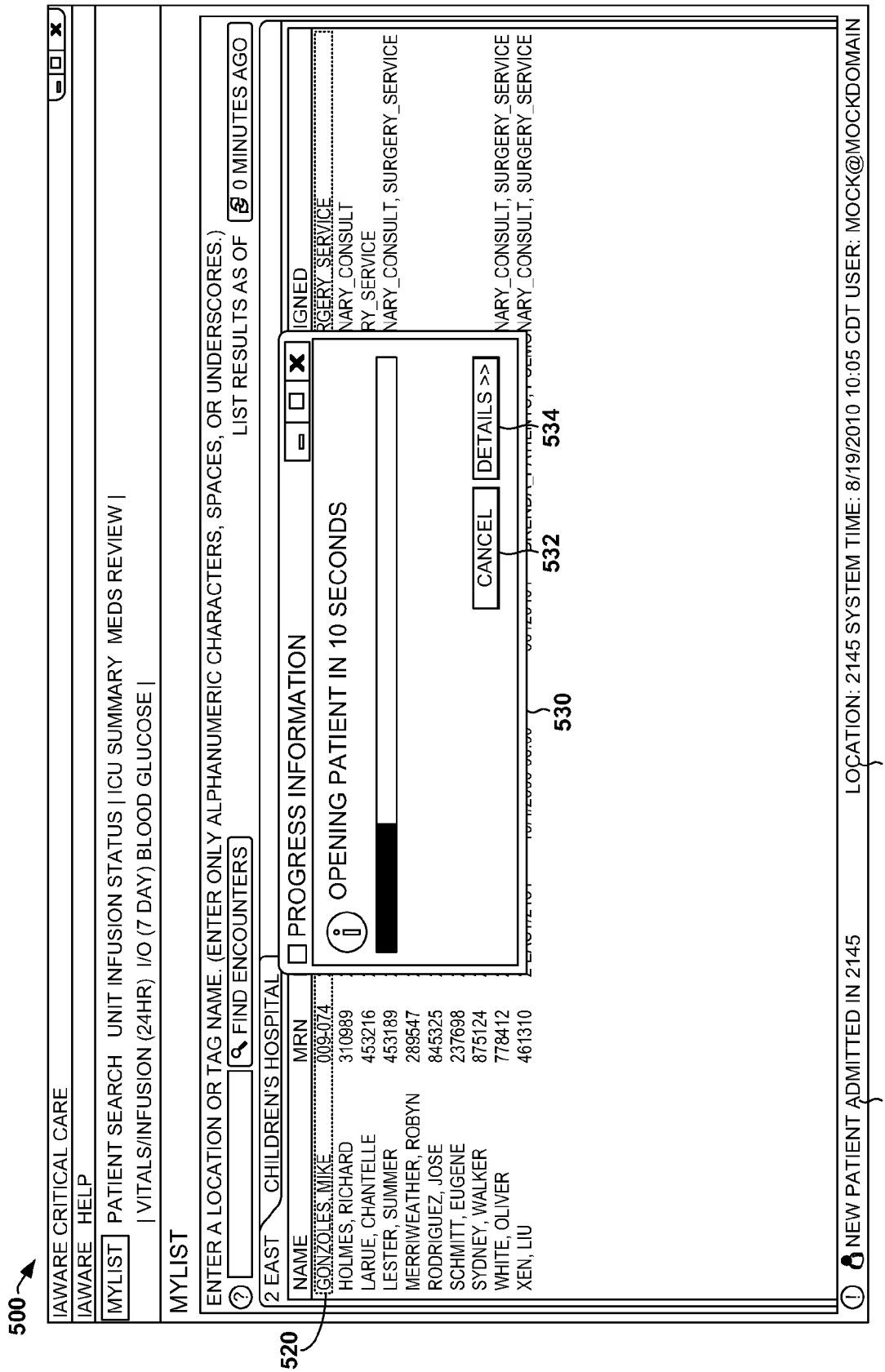

Referring now to FIG. 5, in an illustrative screen display 500, the admission display area 510 displays admission information for a patient that has been admitted to a room in a healthcare facility, as described above. A location display area 515 displays the location of the graphical display device. As described above, a list of patients display area 520 may also be displayed, in various embodiments, identifying patients in a particular location or vicinity, or patients assigned to a particular clinician. An opening progress information message display area 530 displays a progress information message notifying the clinician that information for the patient will be opened and provides the clinician an opportunity, such as with a cancel button 532, to cancel opening the information if the clinician is not ready. In another embodiment, a details button 534 enables the clinician to see additional details corresponding to the patient whose information is being opened.

Figure 6:
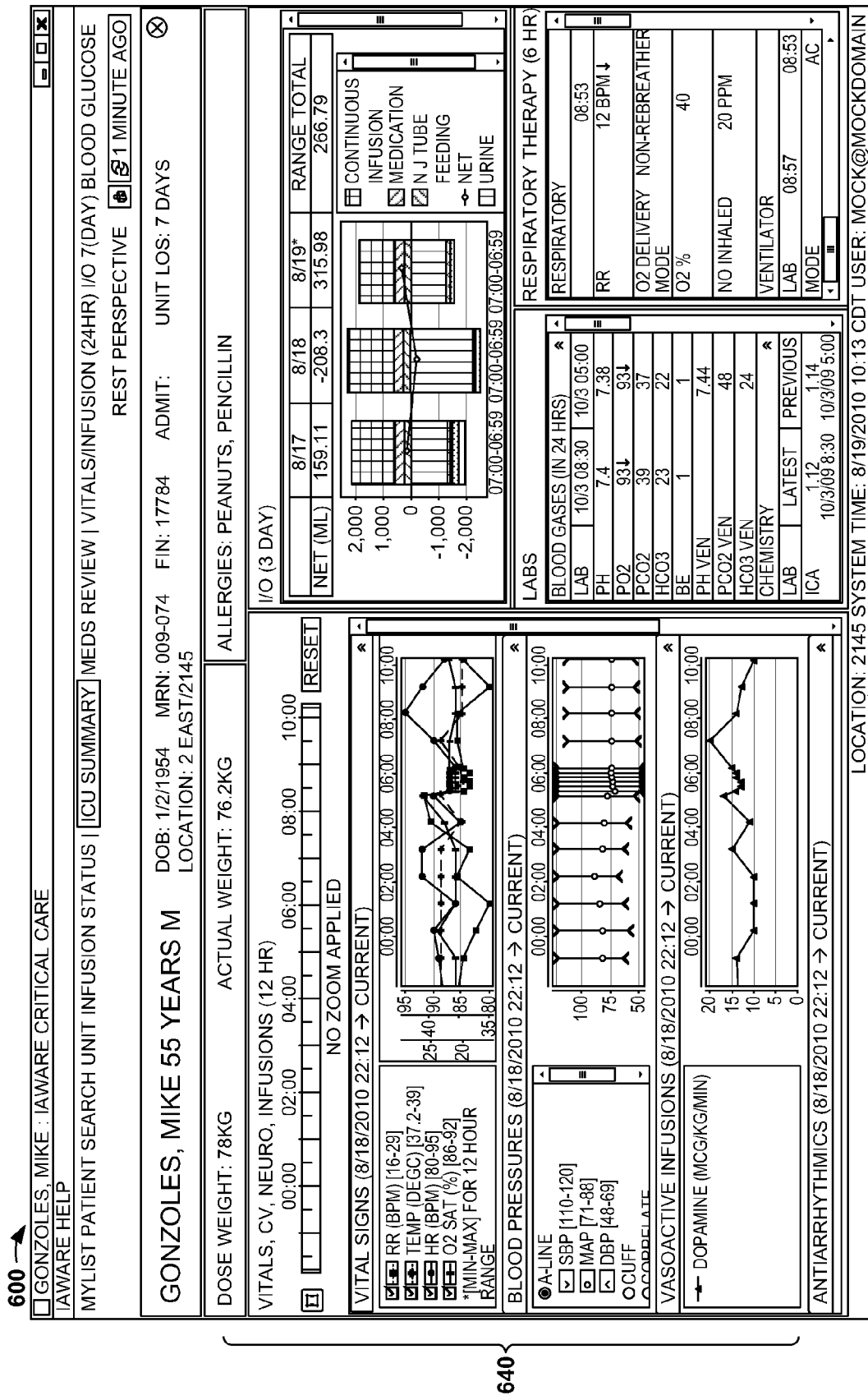

Referring now to FIG. 6, in an illustrative screen display 600, the admission display area 610 displays admission information for a patient that has been admitted to a room in a healthcare facility, as described above. A location display area 615 displays the location of the graphical display device. A patient information area 640 displays information for the patient. In one embodiment, the information is arranged or tailored based upon the treatment the patient is receiving. In another embodiment, the information is arranged or tailored based upon the unit the patient has been admitted to. In another embodiment, the information is arranged or tailored based upon the preference of the clinician assigned to the patient. In one embodiment, the information is a subset of the information contained in the EMR. In one embodiment, the information is arranged or tailored for the purpose of patient and family education. For example, the clinician may wish to display a portion of the information available to illustrate a point to or communicate with the patient or family.

Figure 7:
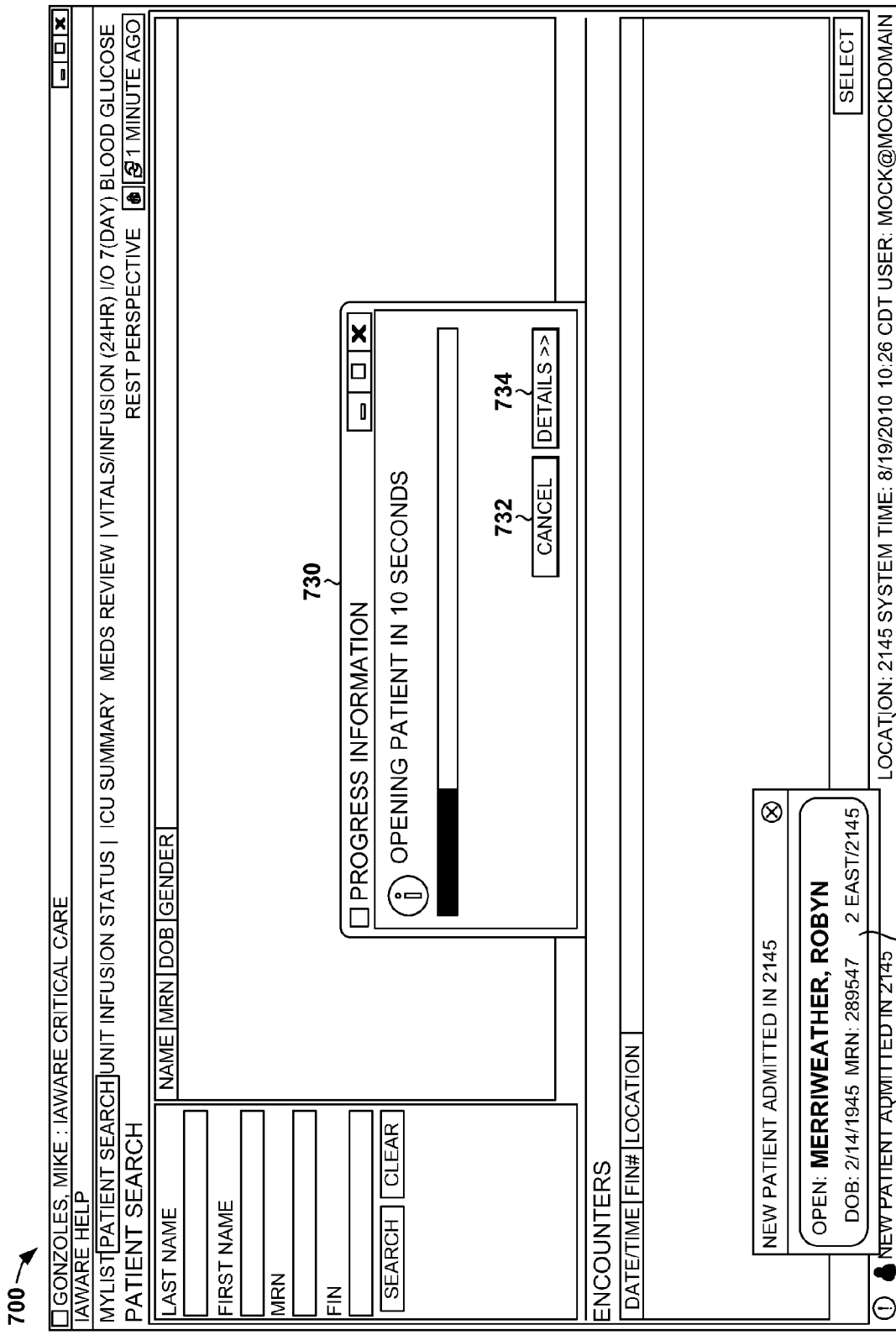

Referring now to FIG. 7, an illustrative screen display 700 shows an embodiment of the present invention from a patient search screen. Rather than the clinician having to search for a particular patient, the admission display area 710 displays admission information for a patient that has been admitted to a room in a healthcare facility. As described above, additional information 712 is available and displayed to a clinician by moving a cursor over or selecting the admission display area 710. A location display area 715 displays the location of the graphical display device. An opening progress information message display area 730 displays a progress information message notifying the clinician that information for the patient will be opened and provides the clinician an opportunity, such as with a cancel button 732, to cancel opening the information if the clinician is not ready. In another embodiment, a details button 734 enables the clinician to see additional details corresponding to the patient whose information is being opened.

Figure 8:
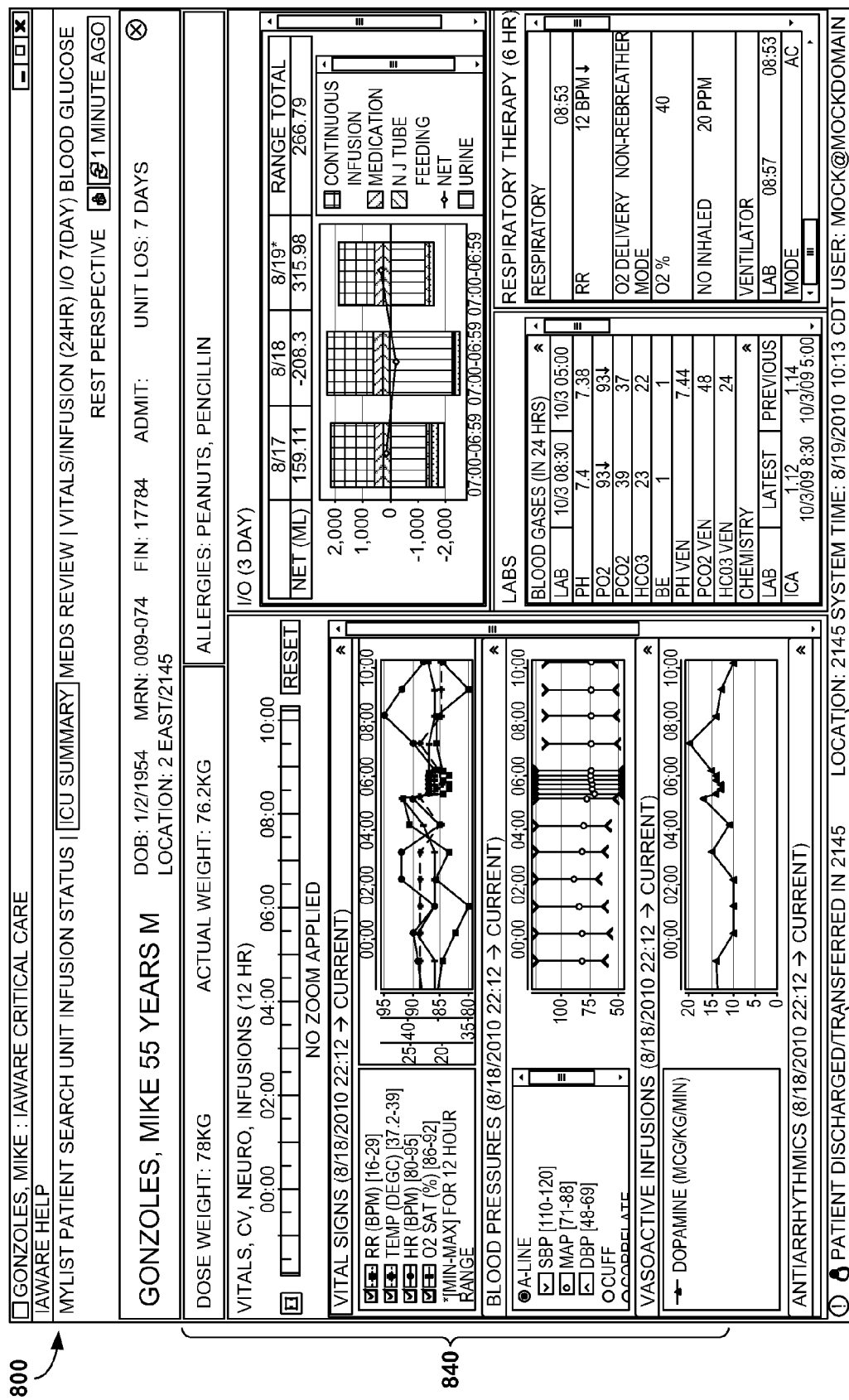

Referring now to FIG. 8, in an illustrative screen display 800, a patient information area 840 displays information for the patient, as described above. A discharge or transfer notification display area 850, in various embodiments, displays a notification that a patient has been discharged or transferred. A location display area 815 displays the location of the graphical display device.

Figure 9:

Referring now to FIG. 9, in an illustrative screen display 900, a patient information area 940 displays information for the patient, as described above. A discharge or transfer notification display area 950, in various embodiments, displays a notification that a patient has been discharged or transferred. A closing progress information message display area 960 displays a progress information message notifying the clinician that information for the patient will be closed and provides the clinician an opportunity, such as with a cancel button 962, to cancel closing the information if the clinician is not finished reviewing or editing the information.

In another embodiment, a details button 964 enables the clinician to see additional details corresponding to the patient whose information is being closed. In another embodiment, if the clinician continues reviewing or editing the information for the patient that is not registered to the room, a reminder is displayed to remind the clinician to close the information when the clinician is finished reviewing or editing the information. A location display area 915 displays the location of the graphical display device.

Figure 10:
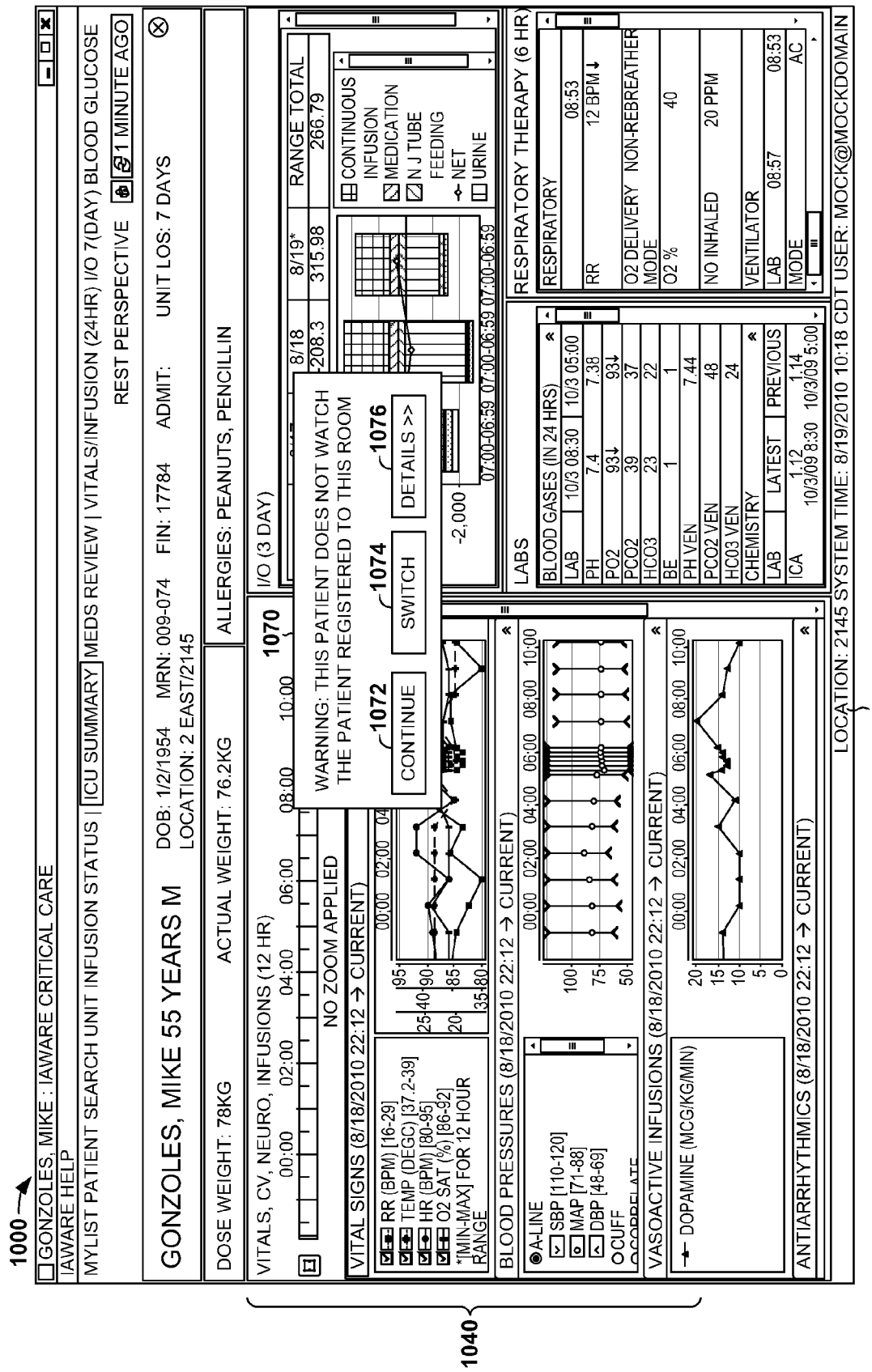

Referring now to FIG. 10, in an illustrative screen display 1000, a patient information area 1040 displays information for the patient, as described above. In one embodiment, a warning 1070 is displayed if the information does not match the patient registered to the room. A continue button 1072 allows the clinician to continue reviewing or editing the information for the patient not registered to the room. A switch button 1074 allows the clinician to switch to the patient currently registered to the room and review or edit that patient's information. A details button 1076 provides additional details, such as where the patient whose information is currently displayed has been transferred to, or discharge information, if that patient has been discharged. The additional details may also include details corresponding to the patient who is currently registered to the room. A location display area 1015 displays the location of the graphical display device.

Figure 11:
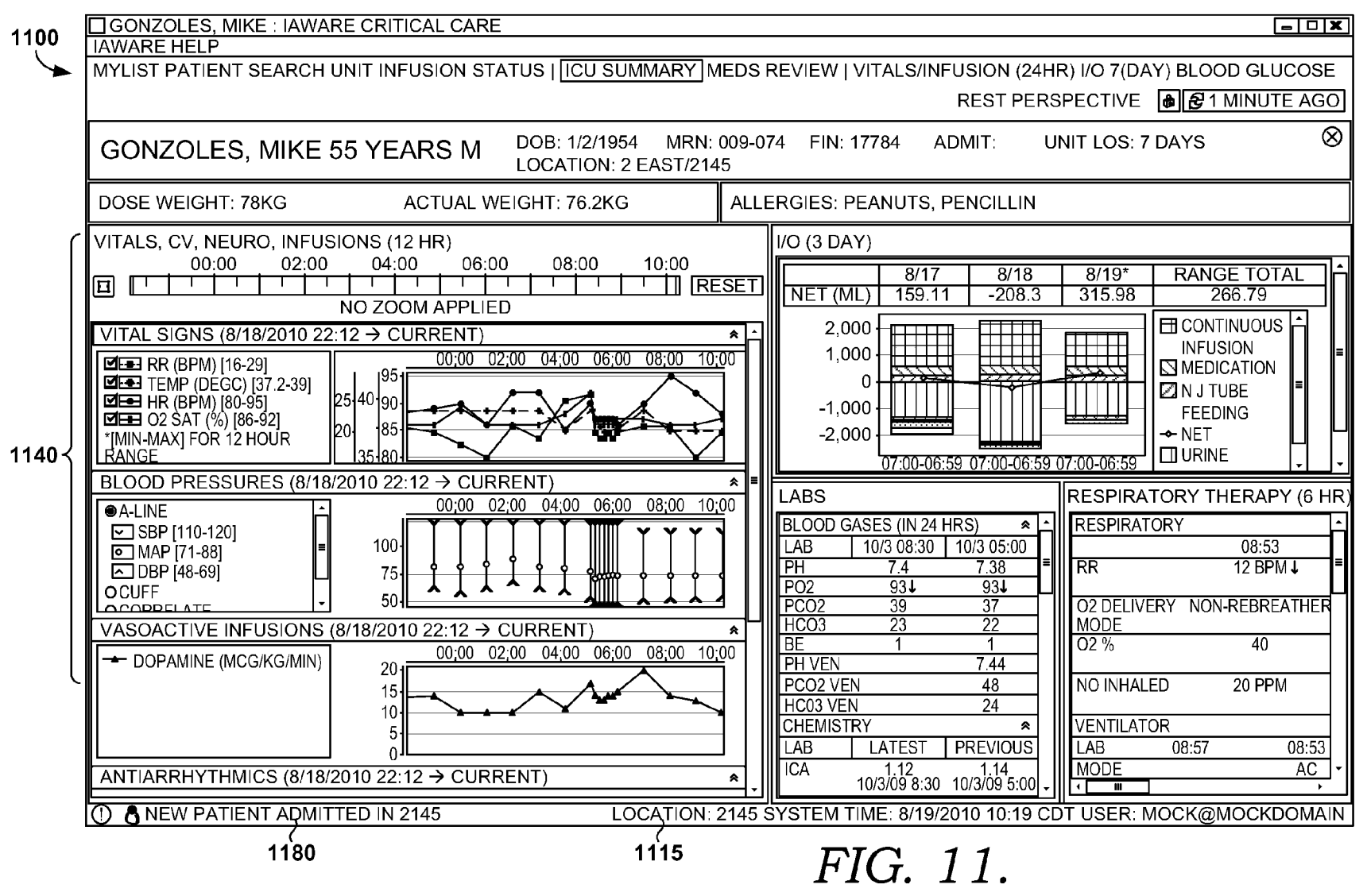

Referring now to FIG. 11, an illustrative screen display 1100, a patient information area 1140 displays information for the patient, as described above. A location display area 1115 displays the location of the graphical display device. A new patient admission display area 1180 displays new patient admission information for a new patient that has been admitted to a room in a healthcare facility. In one embodiment, the new patient admission information is for a new patient that has been admitted to the room the clinician is currently in. In another embodiment, the new patient admission information is for a new patient the clinician is assigned to.

Figure 12:

Referring now to FIG. 12, additional information 1282 is available and displayed to a clinician by moving a cursor, in one embodiment, over the new patient admission display area 1280. In another embodiment, the additional information is displayed to the clinician when the clinician selects the new patient admission display area 1280. In one embodiment, the additional information may include an option to switch to and open the new patient information associated with the new patient such that when the clinician selects the new patient or clicks in an appropriate section, such as a switch to button 1284, of the additional information, the new patient information for the new patient opens. In another embodiment, the additional information may include an option to keep the information open for the previous patient, such as by clicking a keep button 1286. The information for the patient that has been discharged or transferred remains open until the clinician is finished reviewing or editing that patient's information. A location display area 1215 displays the location of the graphical display device.

Figure 13:

Referring now to FIG. 13, an illustrative screen display 1300, a patient information area 1340 displays information for the patient, as described above. A new patient admission display area 1380 displays new patient admission information for a new patient that has been admitted to a room in a healthcare facility. An opening progress information message display area 1330 displays a progress information message notifying the clinician that new patient information for the new patient will be opened and provides the clinician an opportunity, such as with a cancel button 1332, to cancel opening the information if the clinician is not ready. In another embodiment, a details button 1334 enables the clinician to see additional details corresponding to the new patient whose information is being opened or to the patient whose information is currently displayed. A location display area 1315 displays the location of the graphical display device.

Figure 14:
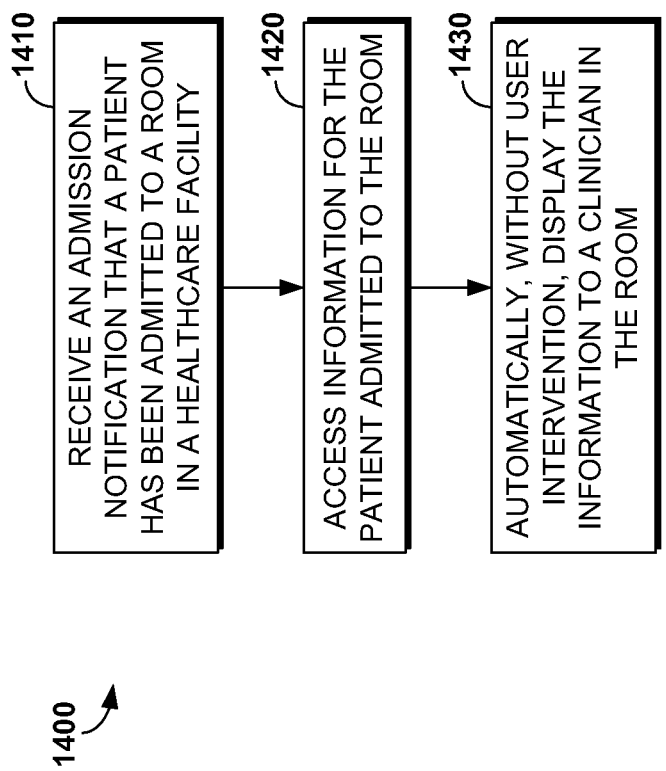
FIG. 14 is a flow diagram of a method in accordance with an embodiment of the present invention.

Referring now to FIG. 14, an illustrative flow diagram 1400 is shown of a method for automating displays based on admissions, discharges, and transfers data. At step 1410, an admission notification that a patient has been admitted to a room in a healthcare facility is received. Information for the patient admitted to the room is accessed at step 1420. In one embodiment, the location of the graphical display device is determined. The information, at step 1430, is displayed automatically, without user intervention, to a clinician in the room.

In one embodiment, it is determined that a clinician is ready to view the information for the patient. In another embodiment, the clinician is prompted. Input from the clinician indicates that the clinician is not finished with the information for a previous patient and the information is kept open until the information is manually closed by the clinician or until a preconfigured time has lapsed. After the clinician manually closes the information for the previous patient the clinician is ready to view the information for the patient recently admitted.

In one embodiment, a delay can be set that keeps the information open until a preconfigured time has lapsed after the previous patient has been discharged. In another embodiment, a delay can be set that waits until a preconfigured time has lapsed after a patient has been admitted until the information for that patient is opened.

For example, the clinician may still be reviewing or inputting information for a previous patient. In this example, the clinician may not be ready to view the information for the patient being admitted to the room. The information for the previous patient remains open until the preconfigured time has lapsed or until the clinician closes the information manually. This allows the clinician sufficient time to finish reviewing or inputting information for the patient that was discharged or transferred.

In one embodiment, the clinician is reminded to close the information when the patient is transferred or discharged. In addition to preventing a clinician from reviewing the wrong patient's information, this reminder also helps preserve patient privacy and confidentiality. In one embodiment, the information closes regardless of whether the clinician has manually closed the information. In addition to preventing a clinician from reviewing the wrong patient's information, this reminder and auto-close functionality also helps preserve patient privacy and confidentiality.

In one embodiment, a discharge or transfer notification that the patient has been discharged or transferred is received. In one embodiment, the clinician is prompted. Input from the clinician indicates that the clinician is finished with the information and the information is closed automatically.

In one embodiment, notification that a new patient has been admitted is received. The information of the patient is closed and new information associated with the new patient is opened. In one embodiment, the information of the patient is automatically closed. In one embodiment, the clinician is able to select whether to keep the information of the patient open or switch to the new information of the new patient.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The invention claimed is:

1. One or more non-transitory computer storage media having computer-executable instructions embodied thereon that, when executed, facilitate a method of automating displays based on admissions, discharges, and transfers, the method comprising:
   receiving an admission notification, from an admission, discharge, and transfer system, that a patient has been admitted to a room in a healthcare facility;
   automatically, based on the receiving an admission notification, retrieving an electronic medical record (EMR) for the patient corresponding to the admission notification;
   determining that a clinician is ready to view the EMR, the determining that the clinician is ready to view the EMR comprising detecting that the clinician has viewed or edited an EMR of a previous patient within a first time period;
   automatically, based on the determining that the clinician is ready to view the EMR, displaying the EMR for the patient;
   notifying the clinician that the patient has been discharged or transferred;
   determining that the clinician is finished with the EMR, the determining that the clinician is finished with the EMR comprising detecting that the clinician has viewed or edited the EMR for the patient within a second time period; and
   automatically, based on the determining that the clinician is finished with the EMR, closing the EMR for the patient.

2. The media of claim 1 further comprising receiving a discharge or transfer notification that the patient has been discharged or transferred.

3. The media of claim 1, wherein the determining that the clinician is finished with the EMR further comprises:
   prompting the clinician; and
   receiving input from the clinician indicating the clinician is finished with the EMR.

4. The media of claim 1, wherein the determining that the clinician is finished with the EMR comprises:
   prompting the clinician;
   receiving input that the clinician is not finished with the EMR; and
   keeping the information open until the EMR is manually closed by the clinician or until a preconfigured time has lapsed.

5. The media of claim 1 further comprising reminding the clinician to close the EMR when the patient is transferred or discharged.

6. The media of claim 1 further comprising:
   receiving notification that a new patient has been admitted;
   closing the EMR of the patient; and
   opening a new EMR associated with the new patient.

7. The media of claim 1 further comprising notifying the clinician if the EMR does not match the patient that is registered to the room or bed.

8. The media of claim 1, wherein the admission notification originates from an ADT workstation not within the room the patient is being admitted to.

9. A computer system for automating displays based on admissions, discharges, and transfers, the computer system comprising a processor coupled to a computer storage medium, the computer storage medium having stored thereon a plurality of computer software components executable by the processor, the computer software components comprising:
   a notification component for receiving, from an admission, discharge, and transfer system, a notification that a patient has been admitted to a room or bed;
   an information component for retrieving an electronic medical record (EMR) for the patient corresponding to the notification;
   a ready component for determining that a clinician is ready to view the EMR, the determining that the clinician is ready to view the EMR comprising detecting that the clinician has viewed or edited an EMR of a previous patient within a first time period;
   a display component for displaying, without user intervention and based on the notification and the determining that the clinician is ready to view the EMR, the EMR to the clinician;
   a discharge/transfer notification component for notifying the clinician that the patient has been discharged or transferred;
   a finish component for determining that the clinician is finished with the EMR, the determining that the clinician is finished with the EMR comprising detecting that the clinician has viewed or edited the EMR for the patient within a second time period; and
   a close component for automatically closing the EMR for the patient.

10. The system of claim 9, further comprising a not ready component for keeping the EMR open until the clinician is finished.

11. The system of claim 9, further comprising a new patient component for notifying the clinician that a new patient has been assigned to the room or bed.

12. The system of claim 11, further comprising a new information component for automatically displaying a new EMR associated with the new patient.

13. The system of claim 9, further comprising a mismatch component for notifying the clinician if the displayed EMR does not match the patient that is registered to the room or bed.

14. The system of claim 9, further comprising a reminder component for reminding the clinician to close the EMR after the patient is transferred or discharged.

15. One or more non-transitory computer storage media having computer-executable instructions embodied thereon that, when executed, produce a graphical user interface (GUI) to facilitate automating displays based on admissions, discharges, and transfers, the GUI comprising:
   a first display area that displays admission information, received from an admission, discharge, and transfer system, for a patient that has been admitted to a room in a healthcare facility;
   a second display area that automatically displays, based on the receiving the admission information, an opening progress information message notifying the clinician that EMR for the patient will be opened and providing the clinician an opportunity to cancel opening the EMR if the clinician is not ready;

a third display area that automatically displays, based on the patient being admitted to the room and determining that a clinician is ready to view the EMR, the EMR for the patient to the clinician in the room, the EMR automatically being retrieved once the patient has been admitted to the room, the determining comprising detecting that the clinician has viewed or edited an EMR of a previous patient within a first time period;

a fourth display area that displays a notification that the patient has been discharged or transferred from the room or bed; and a fifth display area that automatically displays a closing progress information message, based on determining that the clinician is finished with the EMR, notifying the clinician that EMR for the patient will be closed and providing the clinician an opportunity to cancel closing the EMR if the clinician is not ready, the determining that the clinician is finished with the EMR comprising detecting that the clinician has viewed or edited the EMR for the patient within a second time period.

16. The media of claim 15, further comprising a sixth display area that displays a list of patients assigned to the clinician and highlights the patient registered to the room the clinician is in.

17. The media of claim 15, further comprising a seventh display area that displays a notification that opened EMR does not match the patient that is registered to the room or bed.

18. The media of claim 15, wherein the fourth display area includes a notification of a new patient that has been admitted to the room or bed.

19. The media of claim 18, wherein the fourth display area allows the clinician to keep the EMR open for the patient that has been discharged or transferred or switch to a new patient EMR for the new patient.

* * * * *